United States Patent [19]

Rakoutz

[11] 4,252,985
[45] Feb. 24, 1981

[54] PROCESS FOR THE PREPARATION OF O-METHALLYLOXYPHENOL BY THE SELECTIVE MONOETHERIFICATION OF PYROCATECHOL

[75] Inventor: Michel Rakoutz, Oullins, France

[73] Assignee: Philagro, Lyons, France

[21] Appl. No.: 49,747

[22] Filed: Jun. 18, 1979

[30] Foreign Application Priority Data

Jun. 26, 1978 [FR] France .............................. 78 19826

[51] Int. Cl.$^3$ ............................................. C07C 41/01
[52] U.S. Cl. .................................... 568/652; 568/651; 568/568; 568/766
[58] Field of Search ................................ 568/652, 650

[56] References Cited

U.S. PATENT DOCUMENTS

| 3,274,260 | 9/1966 | Levy et al. | |
| 3,474,171 | 10/1969 | Scharpf | |
| 3,689,570 | 9/1972 | Gradeff et al. | 568/650 |
| 3,927,118 | 12/1975 | Ozretich | 568/652 |

OTHER PUBLICATIONS

Laskina et al., Chemical Abstracts, vol. 61 (1964), 11919 (b-d).
McKillop et al., Tetrahedron, vol. 30 (1974), 1379-1382.

Primary Examiner—Bernard Helfin
Attorney, Agent, or Firm—Browdy and Neimark

[57] ABSTRACT

The process relates to the preparation of o-methallyloxyphenol by the action of methallyl chloride on pyrocatechol in the presence of a basic agent.

It consists in carrying out the reaction in a two-phase liquid reaction medium comprising water and a water-immiscible organic solvent, at a temperature between 50° and 140° C., in the presence of a catalyst chosen from amongst quaternary ammonium derivatives and phosphonium derivatives, using, as the basic agent, an alkali metal or alkaline earth metal hydroxide or an alkali metal carbonate or bicarbonate.

It makes it possible to obtain the monoether selectively by minimizing the formation of diether and of alkylation products of the benzene nucleus of the pyrocatechol.

13 Claims, No Drawings

PROCESS FOR THE PREPARATION OF O-METHALLYLOXYPHENOL BY THE SELECTIVE MONOETHERIFICATION OF PYROCATECHOL

The invention relates to the preparation of o-methallyloxyphenol by the monoetherification of pyrocatechol by means of methallyl chloride.

o-Methallyloxyphenol is a compound which is in itself known and can be used as a starting material for the synthesis of 2,3-dihydro-2,2-dimethylbenzofuran-7-yl methylcarbamate which is a polyvalent insecticidal compound known by the common name of carbofuran. The synthesis of carbofuran from o-methallyloxyphenol has been described in U.S. Pat. No. 3,474,171.

The etherification of monohydroxybenzenes such as phenol does not present any particular difficulties and can be carried out in accordance with several reactions which are in themselves known, such as, e.g.: the action of organic halides or sulphates on alkali metal phenolates.

In the case of dihydroxybenzenes such as pyrocatechol, the selective monoetherification of only one of the two hydroxyl groups present on the benzene nucleus presents serious difficulties because each of the two hydroxyl groups tends to react with the etherifying agent. Significant amounts of diether are therefore generally obtained in addition to the monoether which it is desired to prepare. Thus, if the etherification of pyrocatechol is carried out by means of methallyl chloride, without any special precaution, both o-methallyloxyphenol and significant amounts of 1,2-dimethallyloxybenzene are generally obtained.

Furthermore, the appearance of secondary alkylation reactions of the aromatic nucleus is generally observed in this case, with the attachment of the methallyl radical to this aromatic nucleus and the formation of compounds such as o- and p-methallylpyrocatechols.

The formation of diether and alkylation derivatives of the aromatic nucleus accordingly reduces the yield of monoether and leads to a mixture of compounds, from which it is difficult and expensive to extract the monoether.

An object of the invention is to provide a process which makes it possible to prepare o-methallyloxyphenol with good yields and improved degrees of conversion, compared with the known processes.

U.S. Pat. No. 3,274,260 describes a process for the preparation of monoalkyl ethers of dihydroxybenzenes such as pyrocatechol, in accordance with which process an alkylating agent (alkyl halide, sulphate or toluene-sulphonate) is reacted with the dihydroxybenzene, in the presence of an alkali metal hydroxide, in a two-phase reaction medium comprisng, on the one hand, water, and, on the other hand, a water-immiscible, inert organic solvent, the reaction being carried out at a temperature between about 65° C. and 100° C. In accordance with this process, the monoetherification is carried out in the absence of any catalyst and gives a molar ratio of monoether formed/diether formed of more than 10 and a high yield of monoether, relative to the starting dihydroxybenzene. This process therefore gives good results when using a relatively unreactive etherifying agent such as an alkyl derivative. However, when using an etherifying agent which is more reactive than alkyl derivatives, such as e.g. an allyl derivative like methallyl chloride, which is particularly reactive, the appearance of alkylation reactions of the benzene nucleus is observed and this is very difficult to control (compare French Application No. 2,255,279, page 1, lines 33–36).

Furthermore, it is known, according to Synthesis (8), pages 441–455, 1973, that quaternary ammonium derivatives can be used as phase-transfer catalysts in the case of reactions, such as substitution, elimination, addition etc., which are carried out in a two-phase aqueous-organic reaction medium. According to this reference, this type of catalyst can be used for catalysing various types of substitution reaction such as C-alkylation reactions and O-alkylation reactions.

The present invention is based on the observation that, when methallyl chloride is reacted with pyrocatechol, in the presence of a basic agent, in a two-phase aqueous-organic medium, carrying out the reaction in the presence of a phase-transfer catalyst chosen from amongst quaternary ammonium derivatives and phosphonium derivatives, in accordance with the conditions claimed in the present application, unexpectedly favours the etherification reaction and, more particularly, the monoetherification reaction, the latter becoming very largely predominant, at the expense of the alkylation reaction of the benzene nucleus, whereas, in the absence of catalyst, it is the alkylation reaction of the benzene ring which is largely predominant.

The process for the preparation of o-methallyloxyphenol according to the invention consists in reacting methallyl chloride with pyrocatechol in the presence of a basic agent, in which process the reaction is carried out in a stirred, two-phase liquid reaction medium which comprises water and a water-immiscible, inert organic solvent having a boiling point above 50° C. in the presence of a catalyst chosen from amongst quaternary ammonium derivatives and phosphonium derivatives, at a temperature between 50° C. and 140° C., optionally under pressure, using, as the basic agent, a compound chosen from amongst alkali metal or alkaline earth metal hydroxides and alkali metal carbonates or bicarbonates.

The process according to the invention makes it possible simultaneously to achieve:

a molar ratio of monoether formed/diether formed which is always more than 10 and in certain cases more than 50, a degree of conversion of the pyrocatechol which is always equal to at least 50% and in certain cases more than 80%, and a yield of monoether, calculated relative to the pyrocatechol converted, which is always equal to at least 60% and in certain cases more than 80%, whilst restricting the formation of alkylation products of the benzene nucleus to an acceptable level.

According to the invention, the amount of methallyl chloride to be used must be such that the molar ratio of methallyl chloride/starting pyrocatechol is equal to at least 0.6 and preferably equal to at least 1. The upper limit of this ratio is not critical and it is possible to carry out the reaction in the methallyl chloride which acts both as the reactant and as the water-immiscible solvent. In the case where a solvent other than methallyl chloride is used, and where the latter therefore acts solely as the reactant, good results are obtained by using 0.6 to 2 mols of methallyl chloride per mol of pyrocatechol. The organic solvent must necessarily be inert and water-immiscible and have a boiling point above 50° C. and preferably above 70° C. It can be chosen from amongst the following families of chemicals: aliphatic hydrocarbons such as e.g.: cyclohexane, n-hexane, n-heptane, n-octane and methylcyclohexane, aromatic hydrocarbons such as e.g. toluene, o-, m-or p-xylene, ethylbenzene and benzene, halogenohydrocarbons such as e.g.: 1,2-dichloroethane, trichloroethylene, perchloroethylene, methallyl chloride, chlorobenzene, o-, m-or p-dichlorobenzene and trichlorobenzene, alcohols such as e.g.: n-amyl alcohol, n-hexyl alcohol, isoamyl alcohol, 2-ethylhexan-1-ol, octan-1-ol and 2-ethylbutan-1-ol, ethers such as e.g.: di-n-propyl ether, butyl ether, anisole, phenetol, dibenzyl ether, diphenyl ether, veratrole and diisopropyl ether, ketones, such as e.g.: 4-methylpentan-2-one, acetophenone and methyl isobutyl ketone, and nitriles such as e.g.: benzonitrile and propionitrile.

In practice, good results are obtained by using anisole.

In the reaction medium, the respective amounts of water and organic solvent to be used are not critical and can vary within very wide limits. In practice, good results are obtained by using a reaction medium containing from 1 to 4 parts by volume of organic solvent per part of water. Although the invention mainly relates to the use of a reaction medium containing water and only one organic solvent, it is nevertheless possible, without going outside the scope of the invention, to replace the organic solvent by a mixture of water-immiscible, inert organic solvents which are stable under the reaction conditions and have boiling points above 50° C.

Any derivative known as a catalyst in phase-transfer catalysis reactions can be used as the quaternary ammonium derivative or phosphonium derivative.

The quaternary ammonium derivatives which can be used as catalysts according to the present invention preferably correspond to the general formula:

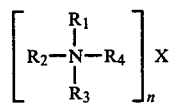
(I)

in which: $R_1$, $R_2$, $R_3$ and $R_4$, which are identical or different, each represent an alkyl radical containing from 1 to 20 carbon atoms, a cycloalkyl radical containing from 3 to 6 carbon atoms, an alkenyl radical containing from 2 to 20 carbon atoms, a hydroxyalkyl radical containing from 1 to 20 carbon atoms, or an optionally substituted phenylalkyl radical in which the alkyl part contains from 1 to 6 carbon atoms, X represents a chlorine, bromine or fluorine atom, a radical $SO_4$, $SO_4H$ or $PO_4H_2$, a hydroxyl radical, an alkoxysulphonyloxy radical containing from 1 to 4 carbon atoms (such as a methoxysulphonyloxy or ethoxysulphonyloxy radical), an alkanesulphonyloxy radical containing from 1 to 4 carbon atoms (such as a methanesulphonyloxy or ethanesulphonyloxy radical), an arenesulphonyloxy radical (such as a benzenesulphonyloxy or p-toluenesulphonyloxy radical) or an alkanoyloxy radical containing from 1 to 4 carbon atoms (such as an acetyloxy or propionyloxy radical), and n is a number equal to the valency of X.

Good results have been obtained by using, as the catalyst, mixtures of quaternary ammonium derivatives, such as those currently marketed under the following trademarks:

Adogen 464: a mixture of methyltrialkylammonium chlorides in which the alkyl parts contain from 8 to 10 carbon atoms, and Cemulcat K 012: a mixture of dihydroxyethyldialkylammonium chlorides in which the alkyl parts contain from 16 to 18 carbon atoms.

Ammonium derivatives of the formula:

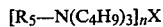

in which: X and n have the same meaning as in the formula I and $R_5$ represents an alkyl radical containing from 1 to 4 carbon atoms, such as ethyltributylammonium chloride, methyltributylammonium chloride, tetrabutylammonium chloride or tetrabutylammonium bisulphate, are preferably used as the catalyst.

The phosphonium derivatives which can be used as the catalyst according to the present invention preferably correspond to the formula:

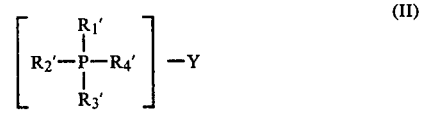
(II)

in which: $R'_1$, $R'_2$, $R'_3$ and $R'_4$, which are identical or different, each represent an alkyl radical containing from 2 to 8 carbon atoms, and Y represents a chlorine or bromine atom.

The amount of catalyst used can vary within very wide limits ranging from 0.01 mol to 1 mol per equivalent of basic agent used. In practice, for economic reasons, 0.10 to 0.25 mol of catalyst is used per equivalent of basic agent.

The solvent/catalyst pair is advantageously chosen so that the catalyst and the unreacted pyrocatechol are extracted from the aqueous phase into the organic phase. Particularly valuable results have been obtained by using, in accordance with the conditions of the invention, the anisole/tributylethylammonium chloride and anisole/tetrabutylammonium chloride pairs, in which cases, at the end of the reaction, the catalyst can be extracted into the organic phase, then separated from the said phase by simply washing the latter with water, and finally recycled.

The amount of basic agent to be used, expressed in equivalents, must represent from 0.5 to 1.4 equivalents per mol of pyrocatechol, i.e.: from 0.5 to 1.4 mols of basic agent per mol of pyrocatechol, when the basic agent is an alkali metal hydroxide or an alkali metal bicarbonate, or from 0.25 to 0.7 mol of basic agent per mol of pyrocatechol, when the basic agent is an alkaline earth metal hydroxide or an alkali metal carbonate.

In practice, for economic reasons, either sodium hydroxide or sodium carbonate is advantageously employed as the basic agent, from 0.6 to 1.1 mols of sodium hydroxide per mol of pyrocatechol preferably being used in the case of sodium hydroxide, and from 0.3 to 0.55 mol of sodium carbonate per mol of pyrocatechol preferably being used in the case of sodium carbonate. The basic agent can be added to the reaction medium all at once as soon as the reaction has started; however, the basic agent is advantageously added gradually throughout the operation, which makes it possible to control the reaction more satisfactorily.

According to another variant of the process described above, it is possible to carry out the monoetherification of pyrocatechol by only introducing a small proportion of the theoretical amount of pyrocatechol to be used, into the reaction medium as soon as the reaction has started, and then by gradually adding, to the reaction medium, the remainder of the pyrocatechol and the basic agent, separately or in a mixture, throughout the reaction.

These variants of the process described above are included within the scope of the present invention.

The reaction temperature can vary from 50° to 140° C. and is preferably between 70° and 110° C. If this temperature is above 100° C., it is necessary to carry out the reaction under pressure in order to avoid the vaporisation of the water present in the reaction mixture. The duration required for the reaction can vary within very wide limits, but is generally between 2 and 6 hours.

The following examples are given by way of indication in order to illustrate the invention without however limiting it.

EXAMPLE 1

The apparatus used consists of a three-necked round-bottomed flask (250 ml) equipped with a reflux condenser, a stirrer, a thermometer, an argon inlet and an argon outlet.

After having purged the equipment with argon, the following are introduced: pyrocatechol (12.1 g, 0.11 mol), anisole (70 ml), methallyl chloride (13.5 g, 0.15 mol), tetrabutylammonium bisulphate (5.68 g, 0.016 mol) and sodium hydroxide (0.7 g, 0.017 mol).

The mixture is heated to 100° C., whilst stirring and under an argon atmosphere. The introduction of a solution of sodium hydroxide (4 g) in water (20 ml) in the course of 2 hours is then started. When the operation is complete, the dropping funnel is rinsed with distilled water (5 ml). The mixture is left for a further 2 hours under reflux, whilst stirring, and is allowed to cool to ambient temperature. Unconverted methallyl chloride (3.6 g) is determined in the organic phase by means of vapour phase chromatography. Distilled water (70 ml) is added to the reaction mixture and the two layers are separated. The aqueous phase is extracted with ethyl acetate (5×60 ml). The organic phases are combined. Unconverted pyrocatechol (2.0 g) and o-dimethallyloxybenzene (0.70 g) are determined therein by means of vapour phase chromatography. By means of high-speed liquid chromatography, the following are also determined in the organic phase: o-methyallyloxyphenol (12.3 g, 0.075 mol), p-methallylpyrocatechol (1.2 g) and o-methallylpyrocatechol (0.13 g).

According to these results:
degree of conversion of the pyrocatechol: 84%
yields relative to the pyrocatechol converted:

| | |
|---|---|
| o-methallyloxyphenol (monoether) | 82% |
| o-dimethallyloxybenzene | 3.6% |
| p-methallylpyrocatechol | 3% |
| o-methallylpyrocatechol | 0.8% | i.e.:

a molar ratio of monoether formed/diether formed equal to 22,
a yield of monoether, relative to the starting pyrocatechol, equal to 69%.

EXAMPLE 2

The following are introduced into the equipment described above: anisole (35 ml), pyrocatechol (8.25 g, 0.075 mol), methallyl chloride (10 g, 0.11 mol) and tributylethylammonium chloride (2.85 g, 0.011 mol).

The mixture is heated at 85° C., whilst stirring under an argon atmosphere. A sodium hydroxide solution containing NaOH (2 g, 0.05 mol) in distilled water (5.5 ml) is then run in over a period of 2 hours 25 minutes. When the introduction is complete, the mixture is left under these conditions for a further 1 hour 15 minutes. After this time, the aqueous phase is neutral. The stirring and heating are stopped and the mixture is allowed to cool under an argon atmosphere. The precipitate of sodium chloride is filtered off and rinsed with anisole (3×15 ml). The filtrates are combined and decanted. Distilled water (115 ml) and the sodium chloride which has been filtered off are added to the aqueous phase. $Cl^-$ (0.049 g. ion) and $(C_2H_5)(C_4H_9)_3N^+$ ($1.8\times10^{-4}$ g. ions) are determined in this solution.

$Cl^-$ (0.010 g. ion) and $(C_2H_5)(C_4H_9)_3N^+$ (0.010 g. ion) are determined in the organic phase (83 ml).

The tributylethylammonium chloride present in the organic phase can be removed by washing with water. For this purpose, the organic phase (10 ml) is taken and washed once with its volume of distilled water. After decantation, the following are determined:

| In the organic phase: | |
|---|---|
| o-methallyloxyphenol | 6.8 g |
| o-dimethallyloxybenzene | 0.052 g |
| o-methallylpyrocatechol | 0.16 g |
| p-methallylpyrocatechol | 1.07 g |
| pyrocatechol | 2.43 g |
| $Cl^-$ | $0.34 \times 10^{-3}$ g.ion |
| In the aqueous phase: | |
| pyrocatechol | 0.11 g |
| $Cl^-$ | $0.88 \times 10^{-3}$ g.ion |
| According to these results: | |
| degree of conversion of the pyrocatechol yields relative to the pyrocatechol converted: | 69% |
| o-methallyloxyphenol | 77% |
| o-dimethallyloxybenzene | 0.4% |
| o-methallylpyrocatechol | 2% | i.e.:

a molar ratio of monoether formed/diether formed equal to 192,
a yield of monoether, relative to the starting pyrocatechol, equal to 53%.

EXAMPLES 3 TO 11

For these examples, the method used is that of Example 1. In the case of Example No. 4, the reaction is carried out in an autoclave under pressure. The conditions used and the results obtained are recorded in the table below:

| Reactants and reaction conditions | Example No. 3 | Example No. 4 | Example No. 5 | Example No. 6 | Example No. 7 | Example No. 8 |
|---|---|---|---|---|---|---|
| Pyrocatechol (in mols) | 0.15 | 0.15 | 0.11 | 0.15 | 0.11 | 0.15 |
| Methallyl chloride | 0.15 | 0.15 | 0.11 | 0.5 | used as | 0.11 |

-continued

| (in mols) | | | | solvent | | |
|---|---|---|---|---|---|---|
| Basic agent | NaOH | NaOH | NaOH | Na$_2$CO$_3$ | NaOH | NaOH |
| (in mols) | (0.1) | (0.1) | (0.1) | (0.05) | (0.1) | (0.1) |
| Solvent | Anisole | Anisole | Anisole | Chloro-benzene | Methallyl chloride | Chloro-benzene |
| | (70 ml) | (70 ml) | (70 ml) | (70 ml) | (70 ml) | (70 ml) |
| Water (in ml) | 20 | 20 | 20 | 20 | 20 | 24 |
| Quaternary ammonium derivative | Cemulcat KO 12 | ADOGEN 464 | Tetrabutyl-ammonium sulphate | ADOGEN 464 | ADOGEN 464 | ADOGEN 464 |
| | (9.7 g) | (9 g) | (5.68 g) | (9 g) | (9 g) | (9 g) |
| Temperature and duration | 94° C. 4 hours | 130° C. 2 hours 45 mins. | 100° C. 4 hours 20 mins. | 100° C. 5 hours | 70° C. 3 hours 45 mins. | 98° C. 5 hours 50 mins. |
| RESULTS | | | | | | |
| Degree of conversion of the pyrocatechol (%) | 60 | 60 | 67 | 50 | 71.2 | 54 |
| Yields relative to the pyrocatechol converted (%) | | | | | | |
| monoether | 72 | 67 | 84 | 82 | 78.3 | 76.2 |
| diether | 1 | 1 | 4 | 0.8 | 5 | 1.2 |
| o-methallylpyrocatechol | 1.4 | 7 | 1.6 | 4 | 2 | 5.1 |
| p-methallylpyrocatechol | 11.4 | 18 | 9.1 | 15 | 16 | 15 |
| Molar ratio of monoether formed/diether formed | 72 | 67 | 21 | 103 | 16 | 65 |
| Yield of monoether/ starting pyrocatechol, % | 46 | 40 | 56 | 41 | 56 | 42 |

| Reactants and reaction conditions | Example No. 9 | Example No. 10 | Example No. 11 |
|---|---|---|---|
| Pyrocatechol (in mols) | 0.15 | 0.11 | 0.11 |
| Methallyl chloride (in mols) | 0.11 | 0.11 | 0.11 |
| Basic agent | NaOH | NaOH | NaOH |
| (in mols) | (0.1) | (0.1) | (0.1) |
| Solvent | dibutyl ether | 2-ethylhexanol | n-octane |
| | (70 ml) | (70 ml) | (70 ml) |
| Water (in ml) | 20 | 20 | 20 |
| Quaternary ammonium derivative | ADOGEN 464 (9 g) | ADOGEN 464 (9 g) | ADOGEN 464 (9 g) |
| Temperature and duration | 97° C. 4 hours 30 mins. | 99° C. 2 hours 30 mins. | 96° C. 3 hours 30 mins. |
| RESULTS | | | |
| Degree of conversion of the pyrocatechol (%) | 55 | 67 | 65 |
| Yields relative to the pyrocatechol converted (%) | | | |
| monoether | 82 | 79 | 66 |
| diether | 2.2 | 4.4 | 3.5 |
| o-methallylpyrocatechol | 4 | 2.2 | 3.8 |
| p-methallylpyrocatechol | 8.8 | 5.8 | 28 |
| Molar ratio of monoether formed/diether formed | 37 | 18 | 19 |
| Yield of monoether/ starting pyrocatechol, % | 45 | 53 | 43 |

COMPARATIVE EXAMPLE: experiment carried out without using a catalyst

The following are introduced into the equipment described in Example 1: anisole (70 ml), pyrocatechol (16.5 g, 0.15 mol) and methallyl chloride (13.5 g, 0.15 mol).

The mixture is heated to 94° C. under an argon atmosphere and whilst stirring. A solution containing sodium hydroxide (4 g) in distilled water (20 ml) is then run in over a period of 2 hours. The mixture is left for a further 1 hour 15 minutes at this temperature, whilst stirring, and is then allowed to cool to ambient temperature.

Unconverted base (2.7 mg) and Cl$^-$ (0.094 g. ion) are determined in the aqueous phase by means of acidimetry.

Unconverted methallyl chloride (3.85 g) is determined in the organic phase by means of vapour phase chromatography.

The decanted aqueous phase is extracted with ethyl acetate (4×50 ml). The organic extracts are combined and added to the organic reaction phase. The following are determined:

| o-dimethallyloxybenzene | none |
|---|---|
| o-methallyloxyphenol | 4.43 g |

| | |
|---|---|
| o-methallylpyrocatechol | 0.8 g |
| p-methallylpyrocatechol | 10.45 g | which represents, relative to the pyrocatechol converted (64%):

| | |
|---|---|
| o-methallyloxyphenol | 28% |
| p-methallylpyrocatechol | 66% |

This experiment shows that, when the reaction is carried out in a two-phase aqueous-organic medium in the absence of catalyst, the formation of alkylation derivatives of the benzene ring becomes largely predominant, at the expense of the monoetherification reaction.

I claim:

1. A process for the preparation of o-methallyloxyphenol by the action of methallyl chloride on pyrocatechol, in the presence of a basic agent, in a liquid reaction medium comprising an organic solvent, in which process the reaction is carried out in a stirred two-phase reaction medium which comprises water and a water-immiscible, inert organic solvent having a boiling point above 50° C., in the presence of a catalyst, at a temperature between 50° C. and 140° C., using, as the basic agent, a compound selected from the group consisting of alkali metal hydroxides, alkaline earth metal hydroxides, alkali metal carbonates and alkali metal bicarbonates; said catalyst being selected from the group consisting of quaternary ammonium derivatives of the formula:

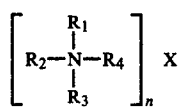

in which: $R_1$, $R_2$, $R_3$ and $R_4$, which are identical or different, each represent alkyl containing 1 to 20 carbons, cycloalkyl containing 3 to 6 carbons, alkenyl containing 2 to 20 carbons, hydroxyalkyl containing 1 to 20 carbons, or optionally substituted phenylalkyl in which the alkyl part contains 1 to 6 carbons; X is chlorine, bromine, fluorine, $SO_4$, $SO_4H$, $PO_4H_2$, hydroxyl, alkoxysulphonyloxy of 1 to 4 carbons, alkanesulphonyloxy of 1 to 4 carbons, arenesulphonyloxy or alkanoyloxy of 1 to 4 carbons; and n is an integer equal to the valency of X; and phosphonium derivatives of the formula:

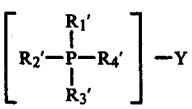

in which: $R'_1$, $R'_2$, $R'_3$ and $R'_4$, which are identical or different, each represent alkyl of 2 to 8 carbons, and Y represents a chlorine or bromine atom.

2. A process according to claim 1, which comprises using from 0.5 to 1.4 equivalents of basic agent and at least 0.6 mol of methallyl chloride per mol of pyrocatechol.

3. A process according to claim 2, in which the basic agent is sodium hydroxide.

4. A process according to claim 3, in which the organic solvent is selected from the group consisting of aliphatic hydrocarbons, aromatic hydrocarbons, halogenohydrocarbons, alcohols, ethers, ketones and nitriles.

5. A process according to claim 4, which comprises using from 0.01 to 1 mol of catalyst per mol of sodium hydroxide.

6. A process according to claim 5, in which the catalyst is a quaternary ammonium derivative of the general formula:

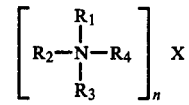

in which: $R_1$, $R_2$, $R_3$ and $R_4$, which are identical or different, each represent an alkyl radical containing 1 to 20 carbon atoms, a cycloalkyl radical containing from 3 to 6 carbon atoms, an alkenyl radical containing from 2 to 20 carbon atoms, a hydroxyalkyl radical containing from 1 to 20 carbon atoms, or an optionally substituted phenylalkyl radical in which the alkyl part contains from 1 to 6 carbon atoms, X represents an atom or radical chosen from amongst chlorine, bromine and fluorine atoms, the radicals $SO_4$, $SO_4H$ and $PO_4H_2$, a hydroxyl radical, an alkoxysulphonyloxy radical containing from 1 to 4 carbon atoms, an alkanesulphonyloxy radical containing from 1 to 4 carbon atoms, an arenesulphonyloxy radical and an alkanoyloxy radical containing from 1 to 4 carbon atoms, and n is an integer equal to the valency of X.

7. A process according to claim 5, in which the catalyst is a phosphonium derivative of the general formula:

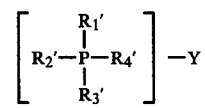

in which: $R'_1$, $R'_2$, $R'_3$ and $R'_4$, which are identical or different, each represent an alkyl radical containing from 2 to 8 carbon atoms, and Y represents a chlorine or bromine atom.

8. A process according to claim 6, in which the organic solvent is anisole.

9. A process according to claim 8, in which the reaction is carried out at a temperature between 70° C. and 110° C., using from 0.6 to 1.1 mols of sodium hydroxide and from 0.6 to 2 mols of methallyl chloride per mol of pyrocatechol.

10. A process according to claim 9, in which the catalyst corresponds to the formula:

$[R_5—N(C_4H_9)_3]_nX$ in which: $R_5$ represents an alkyl radical containing from 1 to 4 carbon atoms.

11. A process according to claim 10, in which the catalyst is ethyltributylammonium chloride, tetrabutylammonium chloride, methyltributylammonium chloride or tetrabutylammonium bisulphate.

12. A process according to any one of claims 1 and 2, in which the basic agent is added gradually to the reaction medium throughout the reaction.

13. A process according to claim 1 or any one of claims 2 to 8, wherein the reaction is carried out at a temperature of 70°–110° C.

* * * * *